United States Patent [19]

Beriger et al.

[11] Patent Number: 5,446,154
[45] Date of Patent: Aug. 29, 1995

[54] PROCESS FOR THE PREPARATION OF AMINOTRIAZINE DERIVATIVES

[75] Inventors: Ernst Beriger, Allschwil; Haukur Kristinsson, Bottmingen, both of Switzerland

[73] Assignee: Ciba-Geigy Corporation, Ardsley, N.Y.

[21] Appl. No.: 221,303

[22] Filed: Mar. 31, 1994

Related U.S. Application Data

[60] Division of Ser. No. 991,672, Dec. 16, 1992, Pat. No. 5,324,842, which is a continuation-in-part of Ser. No. 612,753, Nov. 13, 1990, abandoned.

[30] Foreign Application Priority Data

Nov. 15, 1989 [CH] Switzerland ............ 4107/89

[51] Int. Cl.$^6$ ............................................ C07D 253/06
[52] U.S. Cl. ............................................................ 544/182
[58] Field of Search .............................................. 544/182

[56] References Cited

U.S. PATENT DOCUMENTS 4,931,439 6/1990 Kristinsson .................... 514/242
4,996,325 2/1991 Kristinsson .................... 548/132

FOREIGN PATENT DOCUMENTS 7916515 8/1968 Japan.

OTHER PUBLICATIONS

Chem. Abst., vol. 83:131552t (1975) Hetzheim et al.
Chem. Abst., 67:6449v (1967) Hetzheim et al.
Chem. Abst., 75:129769k (1971) Hetzheim et al.
Chem. Abst., 91:211409g (1979) Takano.
Magnetic Resonance in Chemistry, "hu 15N and $^{13}$C NMR Study, etc" Fritz et al. vol. 28, 331–336 (1990).

*Primary Examiner*—John M. Ford
*Attorney, Agent, or Firm*—Marla J. Mathias

[57] ABSTRACT

The invention relates to a process for the preparation of a compound of formula

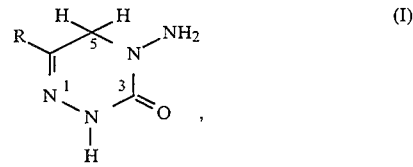

useful as intermediate for the preparation of pesticides, wherein R is hydrogen, $C_1$-$C_6$alkyl, $C_3$-$C_6$cycloalkyl, $C_1$-$C_4$alkyl substituted by from 1 to 10 halogen atoms or by from 1 to 3 radicals selected from the group consisting of $C_1$-$C_3$alkoxy, $C_1$-$C_3$alkylthio and phenyl, phenyl or phenyl substituted by from 1 to 3 radicals selected from the group consisting of halogen, methyl, ethyl, methoxy, methylthio and nitro, which comprises reacting with hydrazine hydrate a compound of formula

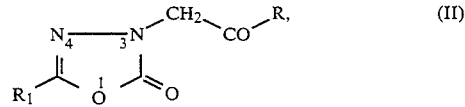

wherein $R_1$ is hydrogen, $C_1$-$C_4$alkyl, $C_3$-$C_6$cycloalkyl, $C_1$-$C_4$alkyl substituted by from 1 to 9 chlorine atoms, $C_1$-$C_3$alkoxy, $C_1$-$C_3$alkylthio, $C_1$-$C_3$alkylsulfonyl, $C_1$-$C_3$alkylsulfonyl, phenyl, phenyl substituted by from 1 to 3 radicals selected from the group consisting of halogen, methyl, ethyl, methoxy, methylthio and nitro, or pyridyl, and subjecting to hydrolysis the resulting compound of formula

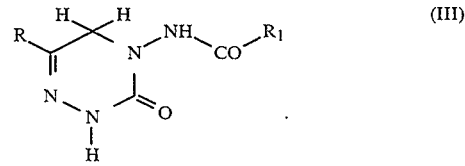

5 Claims, No Drawings

PROCESS FOR THE PREPARATION OF AMINOTRIAZINE DERIVATIVES

This is a divisional of Ser. No. 07/991,672, filed Dec. 16, 1992, now U.S. Pat. No. 5,324,842, which is a continuation-in-part of Ser. No. 07/612,753, filed Nov. 13, 1990, now abandoned.

The present invention relates to a novel process for the preparation of 4-amino-3-oxo2,3,4,5-tetrahydro-1,2,4-triazines, to starting materials and intermediates used in this process and to the use of these starting materials and intermediates in this process.

The invention relates to a process for the preparation of a compound of formula

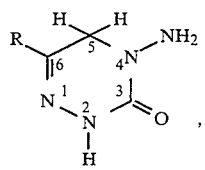

wherein R is hydrogen, $C_1$-$C_6$alkyl, $C_3$-$C_6$cycloalkyl, $C_1$-$C_4$alkyl substituted by from 1 to 10 halogen atoms or by from 1 to 3 radicals selected from the group consisting of $C_1$-$C_3$alkoxy, $C_1$-$C_3$alkylthio and phenyl, phenyl or phenyl substituted by from 1 to 3 radicals selected from the group consisting of halogen, methyl, ethyl, methoxy, methylthio and nitro, which process comprises reacting with hydrazine hydrate a compound of formula

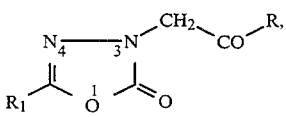

wherein $R_1$ is hydrogen, $C_1$-$C_4$alkyl, $C_3$-$C_6$cycloalkyl, $C_1$-$C_4$alkyl substituted by from 1 to 9 chlorine atoms, $C_1$-$C_3$alkoxy, $C_1$-$C_3$alkylthio, $C_1$-$C_3$alkylsulfinyl, $C_1$-$C_3$alkylsulfonyl, phenyl, phenyl substituted by from 1 to 3 radicals selected from the group consisting of halogen, methyl, ethyl, methoxy, methylthio and nitro, or pyridyl, and R is as defined above; and subjecting the resulting compound of formula

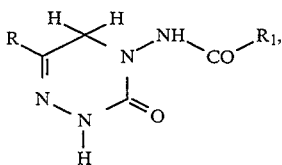

wherein the substituents R and $R_1$ are as defined in formulae I and II, to hydrolysis, preferably acid hydrolysis.

The present process is preferably used for the preparation of compounds of formula I wherein R is methyl, ethyl, isopropyl, tert.-butyl or cyclopropyl. The process is preferably carried out using as starting materials compounds of formula II wherein $R_1$ is $C_1$-$C_4$alkyl.

The aminotriazine derivatives of formula I prepared according to the invention can be used as intermediates for the preparation of 4-[(pyrid-3-yl)-methyleneamino]- or -[(pyrid-3-yl)-methylamino]-3-oxo-2,3,4,5-tetrahydro-1,2,4-triazines, which are distinguished by pronounced insecticidal and acaricidal activity. Such pesticidal compounds are, for example, 4-[(pyrid-3-yl)-methyleneamino]-3-oxo-6-methyl-2,3,4,5-tetrahydro-1,2,4-triazine, 4-[(pyrid-3-yl)-methyleneamino]-3-oxo-6-cyclopropyl-2,3,4,5-tetrahydro-1,2,4-triazine, 4-[(pyrid-3-yl)-methylamino]-3-oxo-6-isopropyl-2,3,4,5-tetrahydro-1,2,4-triazine and 4-[(pyrid-3-yl)-methylamino]-3-oxo-6-tert.-butyl-2,3,4,5-tetrahydro-1,2,4-triazine. Such pesticidal compounds, their preparation and use are described in EP Patent Application No. 314,615.

The process according to the invention can be illustrated by the following reaction scheme, the radicals R and $R_1$ being as defined above.

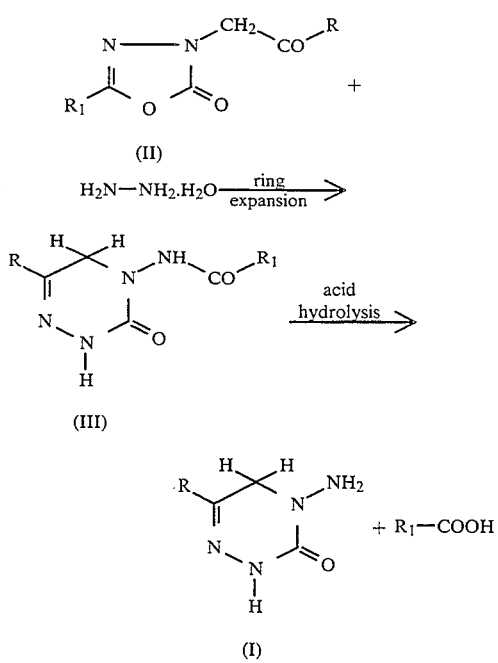

The first step (ring expansion) of the process according to the invention for the preparation of the compounds of formula I is usually carried out under normal pressure and preferably in a solvent. The temperature is from +15° to +120° C., preferably from +20° to +100° C. Suitable solvents are, for example, water, nitriles, such as acetonitrile, alcohols, such as methanol, ethanol or isopropanol, dioxane or tetrahydrofuran. The subsequent hydrolysis of the acylamino compounds of formula III to form the free amino compounds of formula I is preferably carried out with inorganic acids, such as 1N hydrochloric acid to conc. hydrochloric acid or 1N to 10N sulfuric acid, at temperatures of from 0° to +120° C., especially from +20° to +100° C., in an aqueous medium or in organic solvents, such as alcohols, especially methanol or ethanol, dioxane, tetrahydrofuran, nitriles, etc.

The compounds of formula III, wherein R is hydrogen, $C_1$-$C_6$alkyl, $C_3$-$C_6$cycloalkyl, $C_1$-$C_4$alkyl substituted by from 1 to 10 halogen atoms or by from 1 to 3 radicals selected from the group consisting of $C_1$-$C_3$alkoxy, $C_1$-$C_3$alkylthio and phenyl, phenyl or phenyl substituted by from 1 to 3 radicals selected from the group consisting of halogen, methyl, ethyl, methoxy, methylthio and nitro, and $R_1$ is hydrogen, $C_1$-$C_4$alkyl, $C_3$-$C_6$cycloalkyl, $C_1$-$C_4$alkyl substituted by from 1 to 9 chlorine atoms, $C_1$-$C_3$alkoxy, $C_1$-$C_3$alkylthio, $C_1$-$C_3$alkylsulfinyl, $C_1$-$C_3$alkylsulfonyl, phenyl, phenyl substituted by from 1 to 3 radicals selected from the group consisting of halogen, methyl, ethyl, methoxy, methylthio and nitro, or pyridyl, with the proviso, that R is different from unsubstituted phenyl, if $R_1$ is methyl, n-butyl, or unsubstituted phenyl, used as intermediates according to the invention are novel and also form a part of the present invention. Preferred are compounds of formula III, wherein R is methyl, ethyl, isopropyl, tert.-butyl or cyclopropyl, and compounds of formula III, wherein, in consideration of the proviso mentioned hereinbefore, $R_1$ is $C_1$-$C_4$alkyl.

The compounds of formula II, wherein R is hydrogen, $C_1$-$C_6$alkyl, $C_3$-$C_6$cycloalkyl, $C_1$-$C_4$alkyl substituted by from 1 to 10 halogen atoms or by from 1 to 3 radicals selected from the group consisting of $C_1$-$C_3$alkoxy, $C_1$-$C_3$alkylthio and phenyl, phenyl or phenyl substituted by from 1 to 3 radicals selected from the group consisting of halogen, methyl, ethyl, methoxy, methylthio and nitro, and $R_1$ is hydrogen, $C_1$-$C_4$alkyl, $C_3$-$C_6$cycloalkyl, $C_1$-$C_4$alkyl substituted by from 1 to 9 chlorine atoms, $C_1$-$C_3$alkoxy, $C_1$-$C_3$alkylthio, $C_1$-$C_3$alkylsulfinyl, $C_1$-$C_3$alkylsulfonyl, phenyl, phenyl substituted by from 1 to 3 radicals selected from the group consisting of halogen, methyl, ethyl, methoxy, methylthio and nitro, or pyridyl, used as starting materials according to the invention are novel and also form a part of the present invention. Preferred are compounds of formula II, wherein $R_1$ represents $C_1$-$C_4$-alkyl, and compounds of formula II, wherein R is methyl, ethyl, isopropyl, tert.-butyl or cyclopropyl.

The compounds of formula II can be prepared analogously to known procedures, for example as follows (see, for example, EP Patent Application No. 314,615).

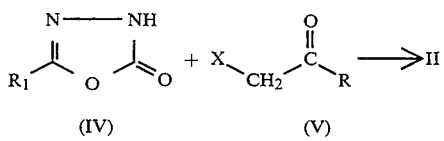

(IV)        (V)

In the above formulae IV and V, R and $R_1$ are as defined above and X is a halogen atom, preferably chlorine or bromine. The process for the preparation of the compounds of formula II is generally carried out under normal pressure, in the presence of a base and in a solvent. The temperature is from 0° to +150° C., preferably from +20° to +100° C. Suitable bases are organic and inorganic bases, for example methylamine, alcoholates, such as sodium methanolate, sodium hydroxide or sodium hydride. Suitable solvents are, inter alia, alcohols, such as methanol and ethanol, halogenated hydrocarbons, for example chloroform, nitriles, for example acetonitrile, tetrahydrofuran, dioxane, dimethyl sulfoxide, dimethylformamide or water.

The compounds of formula IV [see EP Patent Application No. 321,833; J. Pharm. Soc. Japan 76, 1300–1303 (1956); B. 82, 121–123 (1949)] and their preparation, and also the haloketones of formula V, are for the most part known. It is known from Liebigs Ann. Chem. 749, 125 ff. (1971)(C.A. Vol. 75, 129769k, 1971), Z.Chem. 1975, 219 (C.A. Vol. 83, 131552t, 1975) and the German Democratic Republic Patent No. 54369 (C.A. Vol 67, 64449u, 1967) that those 4-amino-6-phenyl-3-oxo-2,3,4,5-tetrahydro-1,2,4-triazines, which fall under the proviso mentioned hereinbefore, can be obtained starting from 2-amino-5-methyl-3-phenacyl-1,3,4-oxadiazolium bromide by reaction with hydrazinc hydrate. The main disadvantage of this process is that it is limited to the preparation of 1,2,4-triazine rings that are phenyl-substituted in the 6-position; in addition, this process comprises several steps and its yield is poor. Furthermore, it is known from EP Patent Application No. 3 14,6 15 to prepare 4-amino-3-oxo-2,3,4,5-tetrahydro-1,2,4-triazines of formula Ia that are substituted in the 6-position by reacting corresponding compounds of formula IIa with an excess of hydrazine in a one-step reaction according to the reaction scheme

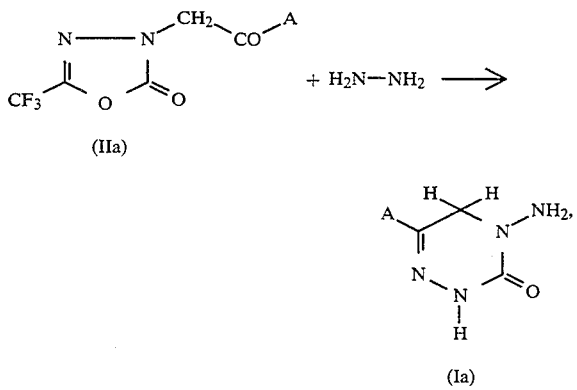

wherein A may be an unsubstituted or substituted alkyl or aryl substituent. The disadvantages of this process are primarily the high cost of the trifluoroacetic acid ethyl ester required for preparing the trifluoroacethydrazide, the instability of that trifluoroacethydrazide at room temperature (Magn. Resonance in Chem., vol. 28, 331, 1990), and the not very high yield in the reaction of the trifluoroacethydrazide with phosgene in water (see Helv. Chim. Acta 1986, 333) to prepare the 2,3-dihydro-2-oxo-5-trifluoromethyl-1,3,4-oxadiazole from which the starting compounds of formula IIa are obtained. Moreover, the reaction according to EP Patent Application No. 314,615 inevitably produces toxic trifluoroacetic acid derivatives as a by-product, which present ecological problems and require a considerable outlay for their disposal.

In contrast, within the scope of the present invention it has now surprisingly been found that the presence of a 5-$CF_3$ group in the starting compounds of formula II is not necessary for the preparation of the 4-amino-3-oxo-2,3,4,5-tetrahydro-1,2,4-triazines of formula I by ring expansion. The present starting compounds of formula II, which contain one of the mentioned radicals $R_1$ in the 5-position instead of the mentioned $CF_3$ group, react readily with hydrazine hydrate to form the acyl-amino compounds of formula III, from which the radical —CO—$R_1$ is subsequently removed by acid hydrolysis to obtain the compounds of formula I. With the process according to the invention, the disadvantages of the procedures hitherto available are eliminated since, in the process according to the invention, inexpensive and readily available starting compounds can be used, high yields are obtained and, instead of toxic trifluoroacetic acid derivatives, ecologically harmless carboxylic acid derivatives, for example acetic acid, are formed as a by-product.

The use of the compounds of formulae II and III in the process according to the invention forms also a part of present invention.

EXAMPLE 1

Preparation of the starting compound 2,3-dihydro-5-methyl-2-oxo-1,3,4-oxadiazol-3-yl-acetone 10 g of 2,3-dihydro-5-methyl-2-oxo-1,3,4-oxadiazole (prepared in customary manner from acethydrazide and phosgene) are added to a solution of 2.3 g of sodium in 100 ml of methanol, the mixture is stirred for a short time and then the solvent is removed in vacuo at a bath temperature of 60° C. The sodium salt so formed is introduced in portions into a solution of 9.2 g of chloroacetone and 0.2 g of tetrabutylammonium bromide in 50 ml of chloroform, and the reaction mixture is stirred for 4 hours at 65° C. After the salts have been filtered off, the solvent is removed in vacuo at a bath temperature of 50° C. The residue is recrystallised from tert.-butyl methyl ether, yielding the title compound having a melting point of 55°–58° C.

The compounds of formula II listed in table 1 can also be prepared in a manner corresponding to that described above.

TABLE 1

| $R_1$ | R | phys. data |
|---|---|---|
| H | —$CH_3$ | b.p. 0.08 torr/80° C. |
| —C($CH_3$)$_3$ | —$CH_3$ | bp. 0.07 torr/102° C. |
| 4-$NO_2$—$C_6H_4$— | —$CH_3$ | m.p. 179–181° C. |
| 2-$NO_2$—$C_6H_4$— | —$CH_3$ | m.p. 98–102° C. |
| 3-$NO_2$—$C_6H_4$— | —$CH_3$ | m.p. 126–129° C. |
| 3,5-di-$NO_2$—$C_6H_3$— | —$CH_3$ | m.p. 116–118° C. |
| 2,4-di-$NO_2$—$C_6H_3$— | —$CH_3$ | m.p. 164–168° C. |
| 3-pyridyl | —$CH_3$ | m.p. 146–148° C. |
| —$CH_3$ | —$CF_3$ | |
| —H | —H | |
| —$CH_3$ | —H | |
| —$CH_3$ | —$C_2H_5$ | |
| —$CH_3$ | —CH($CH_3$)$_2$ | |
| —$CH_3$ | —C($CH_3$)$_3$ | |
| —$CH_3$ | -cyclo-$C_3H_5$ | |
| —$CH_3$ | —$C_6H_5$ | |
| —$CH_3$ | -4-Cl—$C_6H_4$— | |

EXAMPLE 2

Preparation of 4-acetylamino-6-methyl-3-oxo-2,3,4,5-tetrahydro-1,2,4-triazine a) 312 g of 2,3-dihydro-5-methyl-2-oxo-1,3,4-oxadiazol-3-ylacetone in 4 l of ethanol are stirred together with 200 g of hydrazine hydrate for 16 hours at 35° C. The solvent and the excess of hydrazine hydrate are evaporated in vacuo, and the residue is recrystallised from isopropanol to give 148 g (87% of the theoretical amount) of the title compound having a melting point of 197°–199° C.

b) To a solution of 156 g of 2,3-dihydro-5-methyl-2-oxo-1,3,4-oxadiazol-3-ylacetone in 600 ml of isopropanol and 15 ml of water, 75 g of hydrazine hydrate are added at 70° C. over a period of 30 minutes. The mixture is subsequently stirred at reflux temperature for a further 6 hours. 40 g of oxalic acid dihydrate in 160 ml of isopropanol are added, and the precipitate is filtered off, while the mixture is hot, and washed with 150 ml of isopropanol. The filtrate is evaporated in vacuo until the total volume is about 600 ml, then cooled to 0° C. to +5° C., and the precipitated product is filtered off and dried yielding 158 g (93% of the theoretical amount) of the title compound having a melting point of 199°–200° C.

The compounds of formula III listed in table 2 can also be prepared in a manner corresponding to that described above.

TABLE 2

| $R_1$ | R | melting point [°C.] |
|---|---|---|
| H | —$CH_3$ | 185–187 |
| —C($CH_3$)$_3$ | —$CH_3$ | 205–207 |
| 4-$NO_2$—$C_6H_4$— | —$CH_3$ | 252–255 |
| 2-$NO_2$—$C_6H_4$— | —$CH_3$ | 255–257 |
| 3-$NO_2$—$C_6H_4$— | —$CH_3$ | 228–231 |
| 3,5-di-$NO_2$—$C_6H_3$— | —$CH_3$ | 259–262 |
| 2,4-di-$NO_2$—$C_6H_3$— | —$CH_3$ | |
| 3-pyridyl | —$CH_3$ | 259–262 |
| —$CH_3$ | —H | |
| —$CH_3$ | —$CF_3$ | |
| —H | —H | |
| —$CH_3$ | —$C_2H_5$ | |
| —$CH_3$ | —CH($CH_3$)$_2$ | |
| —$CH_3$ | —C($CH_3$)$_3$ | |
| —$CH_3$ | -cyclo-$C_3H_5$ | |
| —$CH_3$ | —$C_6H_5$ | |
| —$CH_3$ | -4-Cl—$C_6H_4$— | |

EXAMPLE 3

Preparation of 4-amino-6-methyl-3-oxo-2,3,4,5-tetrahydro-1,2,4-triazine a) 85 g of 4-acetylamino-6-methyl-3-oxo-2,3,4,5-tetrahydro-1,2,4-triazine in 250 ml of methanol are stirred together with 63 ml of hydrochloric acid (37%) for 4 hours at 50° C. After cooling to 5° C., 250 ml of ice cold water and 125 ml of sodium hydroxide solution (50%) are added. The solvent is removed by evaporation in vacuo. The residue is taken up in 100 ml of ethanol, and the solvent is removed again in vacuo. The residue is taken up in 1200 ml of acetonitrile, undissolved salt precipitates are removed by filtration, the filtrate is concentrated to a small volume, the residue is caused to crystallise by adding 100 ml of acetic acid ethyl ester at 0° C., and the colourless crystals are filtered off and dried yielding 60.4 g (92% of the theoretical amount) of the title compound having a melting point of 118°–120° C.

b) A mixture of 17 g of 4-acetylamino-6-methyl-3-oxo-2,3,4,5-tetrahydro-1,2,4-triazine, 63 ml of hydrochloric acid (37%) and 250 ml of methanol is stirred for 4 hours at 50° C. After cooling to 15° C., 82 g of sodium acetate are added, the mixture is stirred for a further 15 minutes, and the solvent is removed by evaporation. The residue is taken up in 100 ml of ethanol, and the solvent is removed again in vacuo. The residue is taken up in 1200 ml of acetonitrile, undissolved salt precipitates are filtered off, the filtrate is evaporated to dryness, the residue is caused to crystallise by adding 50 ml of acetic acid ethyl ester at ambient temperature, and the crystals are filtered off and dried yielding 54.6 g (85% of the theoretical amount) of the title compound having a melting point of 113°–118° C.

c) A mixture of 1.7 g of 4-acetylamino-6-methyl-3-oxo-2,3,4,5-tetrahydro-1,2,4-triazine and 10 ml of 2N hydrochloric acid is stirred for 5 hours at 80° C. After cooling, 1.7 g of sodium acetate are added, and the mixture is concentrated by evaporation in vacuo at a bath temperature of 60° C. The residue is taken up in ethanol, and salt precipitates are filtered off. The filtrate is concentrated to a small volume and caused to crystallise. The title compound is obtained in the form of colourless crystals having a melting point of 116°–119° C.

The compounds of formula I listed in table 3 can also be prepared in a manner corresponding to that described above.

TABLE 3

| R | m.p. [°C.] |
|---|---|
| —$C_2H_5$ | 143–145° |
| —$C_3H_7(i)$ | 79–81° |
| —$C(CH_3)_3$ | 148–150° |
| cyclopropyl | 94–95° |
| phenyl | 199–202° |
| 4-Cl-phenyl | 208–210° |
| H | |
| —$CF_3$ | |

What is claimed is:

1. A compound of formula

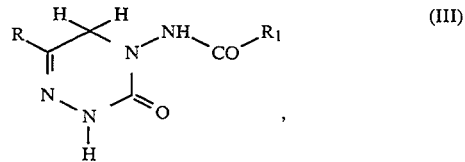

wherein R is hydrogen, $C_1$-$C_6$alkyl, $C_3$-$C_6$cycloalkyl, $C_1$-$C_4$alkyl substituted by from 1 to 10 halogen atoms or by from 1 to 3 radicals selected from the group consisting of $C_1$-$C_3$alkoxy, $C_1$-$C_3$alkylthio and phenyl, phenyl, or phenyl substituted by from 1 to 3 radicals selected from the group consisting of halogen, methyl, ethyl, methoxy, methylthio and nitro, and $R_1$ is hydrogen, $C_1$-$C_4$alkyl, $C_3$-$C_6$cycloalkyl, $C_1$-$C_4$alkyl substituted by from 1 to 9 chlorine atoms, $C_1$-$C_3$alkoxy, $C_1$-$C_3$alkylthio, $C_1C_3$alkylsulfinyl, $C_1$-$C_3$alkylsulfonyl, phenyl, phenyl substituted by from 1 to 3 radicals selected from the group consisting of halogen, methyl, ethyl, methoxy, methylthio and nitro, or pyridyl, with the proviso, that R is different from unsubstituted phenyl, if $R_1$ is methyl, n-butyl or unsubstituted phenyl.

2. A compound of formula III according to claim 1, wherein R represents a radical selected from the group consisting of methyl, ethyl, isopropyl, tert.-butyl and cyclopropyl.

3. A compound of formula III according to claim 1, wherein and $R_1$ is $C_1$-$C_4$alkyl.

4. A compound of formula III according to claim 2, wherein and $R_1$ is $C_1$-$C_4$alkyl.

5. 4-Acetylamino-6-methyl-3-oxo-2,3,4,5-tetrahydro-1,2,4-triazine according to claim 1.

* * * * *